United States Patent [19]

Zorner et al.

[11] Patent Number: 5,284,819
[45] Date of Patent: Feb. 8, 1994

[54] HERBICIDALLY-ACTIVE GLYCOL ESTERS OF FATTY ACIDS

[75] Inventors: Paul S. Zorner, La Costa, Calif.; Yasuko Tsujino, Kangawa; Osamu Kamioka, Yokohama, both of Japan

[73] Assignee: Mycogen Corporation, San Diego, Calif.

[21] Appl. No.: 877,331

[22] Filed: May 1, 1992

[51] Int. Cl.$^5$ .................................. A01N 37/12
[52] U.S. Cl. ................... 504/127; 504/140; 504/142; 504/291; 504/313
[58] Field of Search ............... 71/106; 504/127, 140, 504/142, 291, 313

[56] References Cited

U.S. PATENT DOCUMENTS

| | | | |
|---|---|---|---|
| 2,626,862 | 1/1953 | Zimmerman et al. | 71/113 |
| 4,975,110 | 12/1990 | Puritch et al. | 71/113 |
| 5,035,741 | 7/1991 | Puritch et al. | 71/113 |
| 5,093,124 | 3/1992 | Kulenkampf | 424/406 |

OTHER PUBLICATIONS

Sill, L. Z., P. V. Nelson (1970) "Relationship Between Azalea Bud Morphology and Effectiveness of Methyl Decanoate, a Chemical Pinching Agent," J. Amer. Hort. Sci. 95(3):270-273.

Tso, T. C., G. L. Steffens, M. E. Engelhaupt (1965) "Inhibition of Tobacco Axillary Bud Growth with Fatty Acid Methyl Esters," J. Agr. Food Chem. 13(1):78-81.

*Primary Examiner*—Richard L. Raymond
*Assistant Examiner*—S. Mark Clardy
*Attorney, Agent, or Firm*—Saliwanchik & Saliwanchik

[57] ABSTRACT

The subject invention pertains to novel methods and compositions utilizing novel fatty acid esters which exhibit excellent herbicidal activity in controlling unwanted vegetation. The novel compositions and methods described here facilitate effective weed control using a wide range of fatty acids.

27 Claims, 1 Drawing Sheet

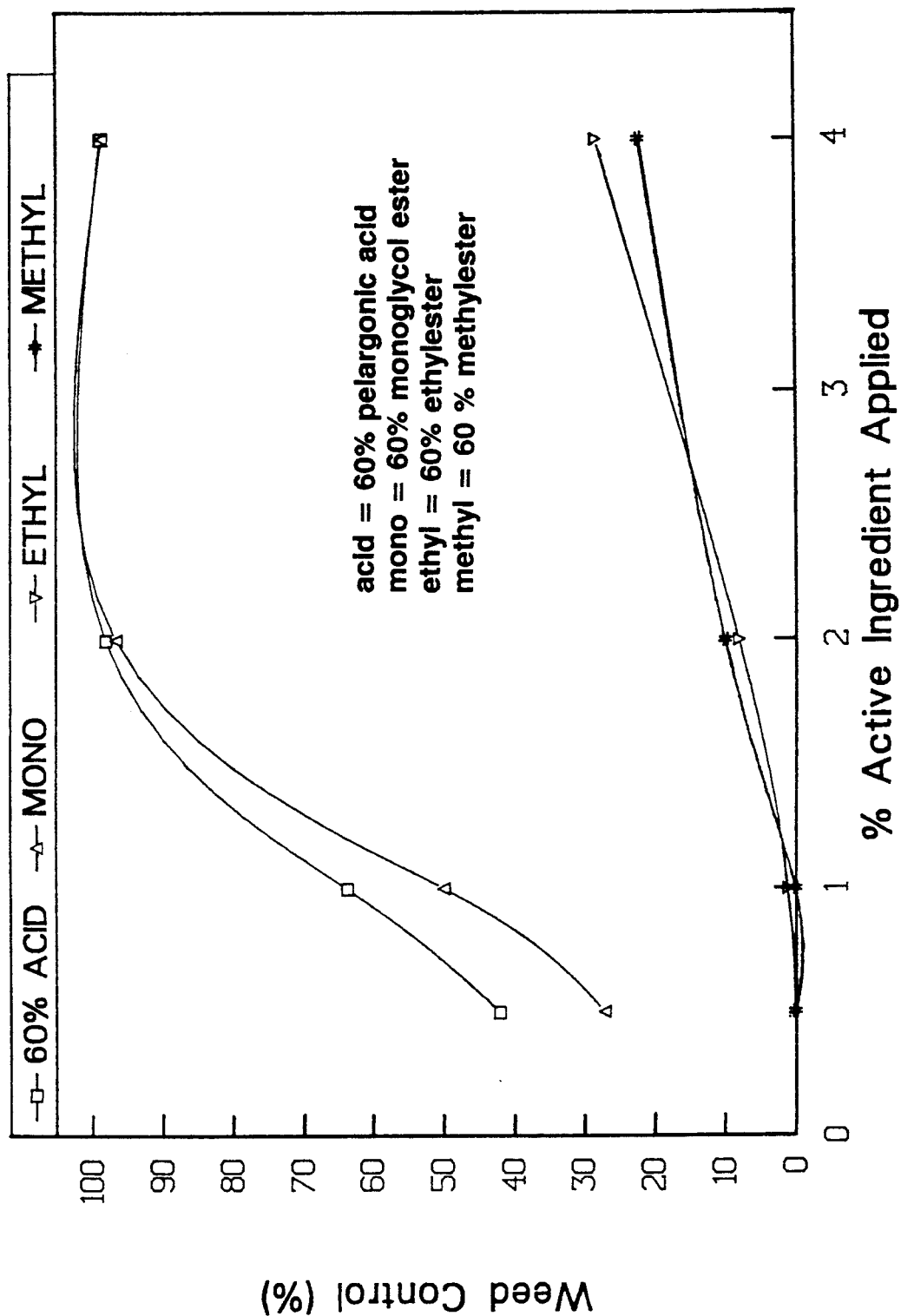

HERBICIDALLY-ACTIVE GLYCOL ESTERS OF FATTY ACIDS

BACKGROUND OF THE INVENTION

Weeds cost farmers billions of dollars annually in crop losses and in the expense of keeping weeds under control. Much of the cost of intertillage of row crops, maintenance of fallow, seedbed preparation, and seed cleaning is chargeable to weed control. Suppression of weeds along highways and railroad right-of-ways, and in irrigation ditches, navigation channels, yards, parks, grounds, and home gardens also is expensive. Ragweed pollen is the source of annual periodic distress to several million hayfever sufferers. Poison ivy, poison oak, poison sumac, nettles, thistles, sandburs, and puncturevine also bring pain to millions. Weeds also serve as hosts for other crop diseases as well as for insect pests.

The losses caused by weeds in agricultural production environments include decrease in crop yield, reduced crop quality, increased irrigation costs, increased harvesting costs, decreased land value, injury to livestock, and crop damage from insects and diseases harbored by the weeds.

Chemical herbicides have provided an effective method of weed control; however, the public has become concerned about the amount of residual chemicals which might be found in food, ground water, and the environment. Stringent new restrictions on the use of herbicides and the elimination of some effective herbicides from the market place could limit economical and effective options for controlling costly weeds. Additionally, the visually apparent phytotoxic effects of some systemic herbicides appear very slowly on the target weeds, so pesticide users often seek methods by which the apparent speed of action of the herbicide is increased.

Recently, salts of fatty acids, primarily sodium or potassium fatty acid salts, have been used commercially as pesticides. Compositions having excellent pesticidal properties which exploit these salts are available commercially from Safer, Inc., under the trademark SAFER INSECTICIDAL SOAP. A herbicidally active composition utilizing partially saponified fatty acids as the active ingredient is sold by Safer, Inc. under the trademark SHARPSHOOTER. These fatty acid compositions are effective, naturally occuring pesticides which have no known long term environmental effects. Although fatty acid salts have herbicidal activity, it would be desirable to provide an alternative composition having an unsaponified active ingredient while maintaining the environmental compatibility of the pesticide and reducing the eye and skin irritancy of the product.

U.S. Pat. Nos. 2,626,862; 4,975,110; and 5,035,741 describe certain fatty acid compositions useful as herbicides. These documents mention the use of salts of fatty acids. Specifically, "saponified" fatty acids are discussed. Saponification means "to form the sodium or potassium salt of a fatty acid." It stems from the soap making industry where animal fats (esters of fatty acids and glycerol) are hydrolyzed in sodium or potassium hydroxide to form the sodium or potassium salts of the fatty acids (soaps) and free glycerol. Mixing sodium or potassium hydroxide with a free fatty acid to form the salt is also called saponification. "Complete" saponification means that 100% of the fatty acid is converted to the salt; "partial" saponification means that <100% of the acid is converted to the salt. This means there is a mixture of the free fatty acid and the fatty acid salt. U.S. Pat. No. 4,975,110 indicates that the free fatty acid form is preferable to fatty acid salts for use as a herbicide. These patents also teach that the proper formulation of a fatty acid herbicide requires one or more surfactants.

In the past, fatty acid esters have been used as chemical pinching agents for the inhibition of bud growth of certain plants (Tso, T. C., G. L. Steffens, M. E. Engelhaupt [1965] J. Agr. Food Chem. 13(1):78-81; Sill, L. P., P. V. Nelson [1970] J. Amer. Soc. Hort. Sci. 95(3):270-273). However, no general herbicidal activity has been established and, in fact, the literature on this subject as well as the common knowledge in the field taught that herbicidal activity of fatty acid compositions was reduced when esters were formed. Therefore, efforts heretofore have focused on methods for formulating fatty acid herbicides to reduce the possibility of any ester formation through, for example, chemical reaction of the fatty acid with free hydroxyl groups. For this reason, esters and ethers have commonly been used as surfactants rather than compounds with free hydroxyl groups.

BRIEF SUMMARY OF THE INVENTION

This invention concerns novel compositions and methods for selective or nonselective control of plants. We have discovered that application to weeds of certain esters of one or more substituted (or unsubstituted) saturated (or unsaturated) fatty acids results in the effective control of a broad range of plants. The fatty acids of the subject invention can be from about C6 to about C20 and can be, for example, in the epoxide, cyclopropane, methylated, or hydroxylated forms. The fatty acid esters of the subject invention can be represented by the following formula:

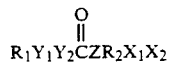

wherein
$Z = O$, N, or S
$R_1 = C5$ to $C19$ saturated or unsaturated hydrocarbon, or an epoxide, or cyclopropane thereof
$Y_1 = H$, C1-C5 hydrocarbon, or hydroxyl at any position along $R_1$
$Y_2 = H$, C1-C5 hydrocarbon, or hydroxyl at any position along $R_1$
$R_2 = C1$ to $C10$ saturated or unsaturated hydrocarbon
$X_1 = H$, or C1 to C3 hydrocarbon at any position along $R_2$
$X_2 =$ hydroxyl at any position on $R_2$ Specifically exemplified herein are saturated fatty acid esters of length C6 to C13 ($R_1 = C5$ to C12). The use of the compositions described here, when used in the proportions and application rates set forth more fully hereinafter, results in an unexpected herbicidal effect. This herbicidal effect is observed over a broader range of carbon chain lengths than is observed for the fatty acids themselves. Also, the herbicidal activity of the esters of the subject invention may, in some circumstances, occur more slowly, which is advantageous in achieving complete control of larger plants. In a preferred embodiment of the subject invention $R_2$ is the mono-glycol ester.

A further aspect of the invention is the use of fatty acid esters in combination with chemical herbicides. The herbicides used according to the subject invention can be systemic herbicides. In one preferred embodiment of the invention, the herbicides may be systemic herbicides with slow uptake rates. The herbicides may or may not be selective. Therefore, using the compositions and procedures of the subject invention, it is possible to achieve enhanced selective control of weeds or enhanced broad range control.

BRIEF DESCRIPTION OF THE DRAWING

FIG. 1 shows a comparison of herbicidal activity of various fatty acid esters.

DETAILED DESCRIPTION OF THE INVENTION

The subject invention pertains to the discovery of certain esters of fatty acids which have advantageous herbicidal properties. The herbicidal esters of the subject invention help to overcome difficulties described in the prior art pertaining to the herbicidal use of fatty acids. The herbicidal activity of fatty acids is well recognized, but it is also known that salts and other derivatives of fatty acids often do not retain the herbicidal activity of the free fatty acid. Specifically, it is known that salts of fatty acids have reduced herbicidal activity compared to free acids and that the preferred herbicidal form is the free fatty acid. It is also widely accepted that herbicidal preparations of fatty acids must be emulsions requiring one or more surfactants. It should be noted that the use of surfactants with fatty acid compositions presents difficulties because it is generally believed that the surfactant must not undergo chemical reaction with the acid. No general herbicidal activity has been established for fatty acid esters and, in fact, the literature on this subject as well as the common knowledge in the field taught that herbicidal activity of fatty acid compositions was reduced when esters were formed. Therefore, efforts heretofore have focused on methods for formulating fatty acid herbicides to reduce the possibility of any ester formation through, for example, chemical reaction of the fatty acid with free hydroxyl groups. Therefore, surfactants with free hydroxyl groups have not been used in fatty acid herbicide formulations due to the potential for formation of an ester between the fatty acid and the surfactant hydroxyl group. Thus, it has been necessary to use an ester or ether as a surfactant.

We have made the surprising discovery that certain esters of fatty acids have excellent herbicidal activity and overcome problems which have heretofore limited the use of fatty acids as herbicides. The esters of the subject invention can be, for example, the mono-glycol ester. Whereas potassium and sodium salts of fatty acids are not highly effective herbicides because of their substantially reduced herbicidal activity compared to the free fatty acid, the esters of the subject invention have excellent herbicidal activity across a wide range of fatty acid chain lengths. Therefore, the chain lengths of fatty acids showing herbicidal activity are not limited, for example, C9. We have found that the esters of fatty acids have herbicidal activity very similar to the free fatty acids.

The fatty acid esters used according to the subject invention can be unsubstituted, or substituted, saturated, or unsaturated, fatty acid esters, of about C6 to about C20. Specifically exemplified are fatty acids of length C6 to C13, as typified by, but not limited to, decanoic and pelargonic acids. The fatty acid ester component of the subject invention may be a single fatty acid ester or a mixture of two or more fatty acid esters.

A further aspect of the subject invention is the use of fatty acid esters in combination with a chemical herbicide to achieve enhanced weed control. The fatty acid esters of the subject invention can be used in combination with a variety of different chemical herbicides. The specific herbicides which should be used for a given application can be readily ascertained by a person skilled in the art. Following is a list of herbicides which may be used according to the subject invention.

| CHEMICAL HERBICIDE FAMILIES AND EXAMPLES | |
| --- | --- |
| HERBICIDE | EXAMPLE |
| 1. Pheoxy acids (acids, esters, salts) | 2,4-D, MCPA, Dichlorprop |
| 2. Benzoic acid | Dicamba |
| 3. Aryloxy phenoxypropionate (acids, esters, salts) | Fluazifop, Dichlofop |
| 4. Sulfonyl ureas (acids, esters) | Chlorimuron, Bensulfuron |
| 5. Imidazilinones | Imazethapyr |
| 6. Bipyridillium | Paraquat |
| 7. Diphenyl ether (acids, salts) | Acifluorfen, Fomesafen |
| 8. Cyclohexanedione | Sethdoxydim, Cycloxydim, Clethodim |
| 9. Methane arsonate | MSMA (Methylarsonic acid) |
| 10. Triazine | Atrazine, Cyanazine |
| 11. Aliphatic carboxylic acids | Dalapon |
| 12. Benzonitrile | Bromoxynil |
| 13. Carbamate | Barban |
| 14. Thiocarbamate | Benthiocarb, Triallate |
| OTHER CHEMICAL HERBICIDES | |
| PYRAZON GLYPHOSATE PICHLORAM METRIBUZIN | |
| GLUFOSINATE CLOPYRALID BENTAZON DESMEDIPHAM | |
| QUINCLORAC AMITROLE PHENMEDIPHAM | |
| TIRCLOPYR ETHIOZIN | |

Herbicides other than those which are specifically listed above may also be used according to the subject invention. In one preferred embodiment of this invention, a fatty acid ester is combined with one or more systemic foliar herbicides with slow uptake characteristics. Specifically, the compositions of the subject invention may advantageously comprise a herbicide from one of the following families: phenoxy acids, aryloxy phenoxypropionates, cyclohexanediones, sulfonyl ureas, and imidazilinones. Of these families, imidazilinones and sulfonyl ureas are particularly advantageous. A further preferred embodiment is the use of a fatty acid with glyphosate.

Specific examples of the chemical herbicides which can be used together with the fatty acid in the composition of the subject invention include, but are not limited to, glyphosate (N-[phosphonomethyl]glycine, isopropylamine salt), imazethapyr, imazapyr ([±],-2-[4,5-dihydro-4-methyl-4-[1-methyl ethyl]-5-oxo-1H-imidazol-2-yl]-3-pyridinecarboxylicacid),sethoxydim(2-[1-[ethoxyimino]butyl]-5-[2-ethyl-thio]propyl]-3-hydroxy-2-cyclohexen-1-one), or paraquat (1,1'-dimethyl-4,4'-bipyridinium dichloride), used alone or optionally with agricultural adjuvants with which the herbicides are normally admixed.

One embodiment of the present invention consists of the application of a tankmix of a fatty acid ester and chemical herbicide. A further embodiment contemplates sequential application of a fatty acid ester and a chemical herbicide.

Materials and Methods

Synthesis of ethylene glycol monoperlargonate. 51.5 g pelargonic acid and 51 g ethylene glycol were dissolved in 200 ml of dichloromethane, and 20 drops of $H_2SO_4$ were added to the mixture. It was stored at room temperature for 6 days. After 6 days, 150 ml of 0.1N NaOH was added to the reaction mixture which was then vigorously shaken. The dichloromethane layer (lower layer) was collected and washed with saturated NaCl solution.

After drying on $Na_2SO_4$, the chloroform layer was evaporated. Remaining oil (38 g) was subjected to vacuum distillation yielding 34.8 g (yield 53.8%) of ethylene glycol monopelargonate (b.p. 135°–137° C. (7 mm Hg)).

Synthesis of the esters of $C_6$ to $C_{14}$ acids.

(a) Hexanoic acid ($C_6$ acid) and heptanoic acid ($C_7$ acid)-each of 100 mmol of $C_6$ and $C_7$ acids were added to 300 mmol of ethylene glycol. Several drops of $H_2SO_4$ were added to the mixture and stored at room temperature for 9 days. Isolation of the esters were carried out using the same procedure as that to isolate ethylene glycol monopelargonate.

(b) Decanoic acid ($C_{10}$ acid), dodecanoic acid ($C_{12}$ acid), and tetradecanoic acid ($C_{14}$ acid)-each of 100 mmol of $C_{10}$, $C_{12}$ and $C_{14}$ acids were dissolved in 50 ml dichloromethane, and 300 mmol of ethylene glycol was added to the solutions. Several drops of $H_2SO_4$ were added to the mixture. The reaction mixtures were stored at room temperature for 9 days. Isolation of the esters were carried out using the same procedure as that to isolate ethylene glycol monopelargonate. Distillations were not undertaken.

Following are examples which illustrate procedures, including the best mode, for practicing the invention. These examples should not be construed as limiting. All percentages are by weight and all solvent mixture proportions are by volume unless otherwise noted.

EXAMPLE 1

Whole plant greenhouse assays were carried out to investigate the herbicidal activity of pelargonic acid, and esters thereof. Barnyardgrass and velvetleaf were mixed planted in 3.9×3.9-inch (10×10 cm) pots in a soil potting mix and were cultivated in the greenhouse that was maintained at daytime temperatures of 25°–30° C. (77°–86° F.), and was watered by sub-irrigation to maintain vigor. Plants were treated at the 2-3 true leaf stage.

MYX 8714, used in the experiments described herein, is a 60% solution of pelargonic acid in ethylene glycol with about 7% nonionic and anionic emulsifiers to provide a stable formulation. The MYX 8714, ethylene glycol monopelargonate (MP), and pelargonic acid (PA) formulations were prepared by diluting the requisite amount of these samples with sufficient water to provide spray mixes which would deliver to the plants the field equivalent of 10.0, 5.0, 2.5, 1.25, 0.63 and 0.32% a.i. w/v of these samples in about 100 gallons/acre of water. For all samples, 1 ml per pot per sample was sprayed. Herbicidal effects were assessed 3, 7 and 10 days after treatment. The weed control ratings representing the extent of control, that is the reduction in growth, were obtained and scored on the basis of 0 to 100, where 100 represents complete plant necrosis and 0 no reduction in growth, as compared to the untreated control.

Table 1 shows the ultimate herbicidal effects of pelargonic acid and esters of pelargonic acid on barnyardgrass and velvetleaf.

TABLE 1

| Conc. (% a.i) | MYX 8714 (% damage) | | PA[3] | | MP[4] | |
|---|---|---|---|---|---|---|
| | BYG[1] | VL[2] | BYG | VL | BYG | VL |
| 10.0 | 99 | 100 | 93 | 100 | 90 | 100 |
| 5.0 | 96 | 100 | 80 | 96 | 85 | 98 |
| 2.5 | 85 | 98 | 65 | 78 | 73 | 85 |
| 1.25 | 72 | 90 | 57 | 33 | 72 | 78 |
| 0.63 | 57 | 47 | 43 | 13 | 47 | 18 |
| 0.32 | 37 | 20 | 3 | 0 | 8 | 3 |
| Seventh day: | | | | | | |
| 10.0 | 98 | 100 | 85 | 100 | 85 | 100 |
| 5.0 | 87 | 199 | 62 | 99 | 77 | 95 |
| 2.5 | 75 | 90 | 43 | 62 | 57 | 68 |
| 1.25 | 40 | 82 | 17 | 37 | 43 | 62 |
| 0.63 | 23 | 40 | 17 | 15 | 10 | 27 |
| 0.32 | 5 | 30 | 0 | 3 | 0 | 7 |
| Tenth day: | | | | | | |
| 10.0 | 98 | 100 | 73 | 100 | 72 | 100 |
| 5.0 | 82 | 100 | 40 | 98 | 47 | 95 |
| 2.5 | 53 | 90 | 20 | 53 | 17 | 57 |
| 1.25 | 27 | 70 | 0 | 27 | 3 | 50 |
| 0.63 | 13 | 37 | 0 | 7 | 0 | 13 |
| 0.32 | 0 | 30 | 0 | 7 | 0 | 3 |

[1]Barnyardgrass.
[2]Velvetleaf.
[3]Pelargonic acid.
[4]Ethylene glycol monopelargonate.

EXAMPLE 2

Effect of Fatty Acid Chain Length

Experiments were conducted to asses the effect of the chain length of the fatty acid ester on herbicidal activity. Mono-glycol esters of C6, C7, C9, C10, C12, and C14 fatty acids were prepared as described in the materials and Methods section above. The esters of these fatty acids were tested as described in Example 1 for their herbicidal activity on velvetleaf and barnyardgrass. Herbicidal activity was assessed at one and three days after treatment.

As can be seen from Table 2, the esters of these fatty acids had excellent herbicidal activity across a wide range of fatty acid chain lengths ranging from C6 to C12.

TABLE 2

Effect of the chain length of fatty acid esters on activity (C6, C7, C9, C10, C12, and C14)

| Conc. | C6 | C7 | C9 | C10 | C12 | C14 |
|---|---|---|---|---|---|---|
| *1 day* | | | | | | |
| velvetleaf | | | | | | |
| 10% | 98 | 100 | 100 | 100 | 95 | 0 |
| 5% | 95 | 96 | 99 | 96 | 82 | 0 |
| 2.5% | 72 | 82 | 96 | 82 | 48 | 0 |
| 1.25% | 8 | 12 | 12 | 68 | 8 | 0 |
| barnyardgrass | | | | | | |
| 10% | 80 | 90 | 100 | 100 | 92 | 0 |
| 5% | 65 | 82 | 99 | 100 | 88 | 0 |
| 2.5% | 45 | 62 | 96 | 98 | 58 | 0 |
| 1.25% | 12 | 30 | 25 | 55 | 30 | 0 |
| *3 day* | | | | | | |
| velvetleaf | | | | | | |
| 10% | 100 | 100 | 100 | 100 | 99 | 0 |
| 5% | 94 | 100 | 100 | 100 | 99 | 0 |
| 2.5% | 42 | 100 | 100 | 100 | 88 | 0 |
| 1.25% | 2 | 8 | 8 | 98 | 90 | 0 |
| barnyardgrass | | | | | | |
| 10% | 100 | 100 | 100 | 100 | 99 | 0 |
| 5% | 95 | 96 | 100 | 100 | 99 | 0 |
| 2.5% | 55 | 42 | 100 | 97 | 48 | 0 |
| 1.25% | 15 | 20 | 35 | 55 | 25 | 0 |

These results with the mono-glycol esters of these fatty acids are in direct contrast to the results obtained using free fatty acids or fatty acid salts of varying chain lengths. As can be seen in Table 3, herbicidal activity is usually at a peak for C9 fatty acids but drops off sharply as the chain length of the fatty acid decreases or increases. $ED_{80}$ is the percentage of active ingredient found to give 80% weed control after raw data is subjected to log-posit regression, a practice commonly used by those skilled in the art. The data were collected as in Example 1 except that the fatty acids were formulated and sprayed in 100% acetone at about 100 gallons/acre. The $ED_{80}$ reported in Table 3 is an average of data collected from application to velvetleaf, barnyardgrass, bromegrass, and pigweed.

Thus, the fatty acid esters of the subject invention are particularly advantageous because they can be used to expand the range of fatty acids which can be used in herbicidal compositions.

TABLE 3

| Compound | ED 80 (%) |
|---|---|
| Hexanoic C6 | 5.34 |
| Heptanoic C7 | 6.55 |
| Octanoic C8 | 2.95 |
| Nonanoic C9 | 2.57 |
| Decanoic C10 | 5.50 |
| Undecanoic C11 | 3.66 |
| Undecenoic C11:1 | 4.53 |
| C12 | very inactive |
| C14 | very inactive |

EXAMPLE 3

Comparison of the Herbicidal Effect of Ethylene Glycol Monopelargonate, Pelargonic Acid Methyl Ester, and Ethyl Ester by Means of Whole Plant Greenhouse Assay Whole plant greenhouse assays were carried out to investigate the concentrations at which ethylene glycol monopelargonate (MP), pelargonic acid methyl ester (C9Me), and pelargonic acid ethyl ester (C9Et) show the most effective herbicidal activity. Barnyardgrass and velvet leaf were mixed planted in $10 \times 10$ cm² pots in a soil potting mix and were cultivated in the greenhouse that was maintained at daytime temperatures of 20°–25° C., and was watered by sub-irrigation to maintain vigor. Plants were treated at the 1.5–3 true leaf stage. The MP, C9Me and C9Et were prepared by diluting the requisite amount of these samples with sufficient water to provide spray mixes which would deliver to the plants the field equivalent of 10.0, 5.0, 2.5, and 1.25% a.i. w/v of these samples in about 100 gallons/acre of water. For all samples, 1 ml per pot per sample was sprayed. Herbicidal effects were assessed 1,3, and 10 days after treatment. The weed control ratings representing the extent of control, that is, the reduction in growth, were obtained and scored on the basis of 0 to 100, where 100 represents complete plant necrosis, and 0 represents no reduction in growth, as compared to the untreated control.

Table 4 shows the ultimate herbicidal effects of MP, C9Me, and C9Et on barnyardgrass and velvetleaf. Similar experiments have been conducted using 60% acid formulation as a standard of comparison. The results of these experiments are shown in FIG. 1.

TABLE 4

Herbicial effect of MP, C9Me, and C9Et at 1, 3, and 10 days after treatment.

| Conc. (% a.i) | MP (% damage) | | C9Me | | C9Et | |
|---|---|---|---|---|---|---|
| | BYG[1] | VL[2] | BYG | VL | BYG | VL |
| *First day:* | | | | | | |
| 10.0 | 99 | 100 | 15 | 30 | 25 | 25 |
| 5.0 | 95 | 100 | 0 | 0 | 0 | 0 |
| 2.5 | 45 | 100 | 0 | 0 | 0 | 0 |
| 1.25 | 25 | 25 | 0 | 0 | 0 | 0 |
| *Third day:* | | | | | | |
| 10.0 | 98 | 100 | 15 | 30 | 20 | 30 |
| 5.0 | 88 | 100 | 0 | 8 | 5 | 8 |
| 2.5 | 45 | 100 | 0 | 0 | 0 | 0 |
| 1.25 | 5 | 15 | 0 | 0 | 0 | 0 |
| *Tenth day:* | | | | | | |
| 10.0 | 98 | 100 | 5 | 20 | 20 | 15 |
| 5.0 | 85 | 100 | 0 | 0 | 3 | 0 |
| 2.5 | 35 | 100 | 0 | 0 | 0 | 0 |
| 1.25 | 8 | 18 | 0 | 0 | 0 | 0 |

[1]Barnyardgrass.
[2]Velvetleaf.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A composition for controlling unwanted vegetation, said composition comprising a monoglycol ester of a monocarboxylic acid, wherein said monocarboxylic acid has about six to about twenty carbon atoms, in a suitable agricultural carrier.

2. The composition, according to claim 1, wherein said fatty acid ester is represented by the following formula:

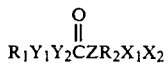

wherein
$Z = O$
$R_1 =$ C5 to C19 saturated or unsaturated hydrocarbon, or an epoxide, or cyclopropane thereof $Y_1$=H, C1–C5 hydrocarbon, or hydroxyl at any position along $R_1$ $Y_2$=H, C1–C5 hydrocarbon, or hydroxyl at any position along $R_1$ $R_2$=C1 to C10 saturated or unsaturated hydrocarbon $X_1$=H, or C1 to C3 hydrocarbon at any position along $R_2$ $X_2$=hydroxyl at any position on $R_2$.

3. The composition, according to claim 2, wherein $R_1$ is C5 to C12.

4. The composition, according to claim 2, wherein $R_1$ is saturated.

5. The composition, according to claim 2, wherein $R_1$ is C8 to C11.

6. The composition, according to claim 5, wherein $R_1$ is C8.

7. The composition, according to claim 1, wherein said ester is the monoglycol ester.

8. The composition, according to claim 1, which comprises a mixture of fatty acid esters.

9. The composition, according to claim 1, which further comprises a surfactant.

10. The composition, according to claim 1, which further comprises a chemical herbicide.

11. The composition, according to claim 10, wherein said herbicide is a foliar herbicide.

12. The composition, according to claim 10, wherein said chemical herbicide is selected from the group consisting of: phenoxy acids, esters, and salts; benzoic acid; aryloxy phenoxypropionate acids, esters, and salts; sulfonyl urea acids and esters; imidazilinones; bipyridillium; diphenyl ether acids and salts; cyclohexanedione; methane arsonate; triazine; aliphatic carboxylic acids; benzonitrile; carbamate; thiocarbamate; pyrazon; glyphosate; pichloram; metribuzin; glufosinate; clopyralid; bentazon; desmedipham; quinclorac; amitrole; phenmedipham; triclopyr; and ethiozin.

13. The composition, according to claim 10, wherein said chemical herbicide is glyphosate.

14. A method for controlling unwanted vegetation, said method comprising applying to said unwanted vegetation, a composition comprising an ester of a monocarboxylic acid, wherein said monocarboxylic acid has about six to about twenty carbon atoms, in a suitable agricultural carrier.

15. The method, according to claim 14, wherein said fatty acid ester is represented by the following formula:

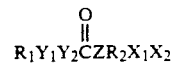

wherein

Z=O $R_1$=C5 to C19 saturated or unsaturated hydrocarbon, or an epoxide, or cyclopropane thereof $Y_1$=H, C1–C5 hydrocarbon, or hydroxyl at any position along $R_1$ $Y_2$=H, C1–C5 hydrocarbon, or hydroxyl at any position along $R_1$ $R_2$=C1 to C10 saturated or unsaturated hydrocarbon $X_1$=H, or C1 to C3 hydrocarbon at any position along $R_2$ $X_2$=hydroxyl at any position on $R_2$.

16. The method, according to claim 15, wherein $R_1$ is C5 to C12.

17. The method, according to claim 15, wherein $R_1$ is saturated.

18. The composition, according to claim 15, wherein $R_1$ is C8 to C11.

19. The method, according to claim 18, wherein $R_1$ is C8.

20. The method, according to claim 15, wherein said ester is the mono-glycol ester.

21. The method, according to claim 14, wherein said composition comprises a mixture of fatty acid esters.

22. The method, according to claim 14, wherein said composition further comprises a surfactant.

23. The method, according to claim 14, wherein said method further comprises applying a chemical herbicide to said unwanted vegetation.

24. The method, according to claim 23, wherein said chemical herbicide is applied simultaneously with said fatty acid ester.

25. The method, according to claim 23, wherein said herbicide is a foliar herbicide.

26. The method, according to claim 23, wherein said chemical herbicide is selected from the group consisting of: phenoxy acids, esters, and salts; benzoic acid; aryloxy phenoxypropionate acids, esters, and salts; sulfonyl urea acids and esters; imidazilinones; bipyridillium; diphenyl ether acids and salts; cyclohexanedione; methane arsonate; triazine; aliphatic carboxylic acids; benzonitrile; carbamate; thiocarbamate; pyrazon; glyphosate; pichloram; metribuzin; glufosinate; clopyralid; bentazon; desmedipham; quinclorac; amitrole; phenmedipham; triclopyr; and ethiozin.

27. The method, according to claim 26, wherein said chemical herbicide is glyphosate.

* * * * *

UNITED STATES PATENT AND TRADEMARK OFFICE
CERTIFICATE OF CORRECTION

PATENT NO.    :   5,284,819

DATED         :   February 8, 1994

INVENTOR(S)   :   Zorner *et al.*

It is certified that error appears in the above-identified patent and that said Letters Patent is hereby corrected as shown below:

Column 2    lines 10-11: Delete "Sill, L.P." and insert --Sill, L.Z.--.

Column 4    ~line 40 (Chart): Delete "Pheoxy" and insert --Phenoxy--.

Column 4    ~line 55 (Chart): Delete "Tirclopyr" and insert --Triclopyr--.

Column 5    line 22: Delete "monoperlargonate" and insert --monopelargonate--.

Signed and Sealed this

Twenty-seventh Day of September, 1994

Attest:

BRUCE LEHMAN

*Attesting Officer*    *Commissioner of Patents and Trademarks*